(12) United States Patent
Feng et al.

(10) Patent No.: US 11,164,345 B2
(45) Date of Patent: Nov. 2, 2021

(54) SYSTEM AND METHOD FOR GENERATING ATTENUATION MAP

(71) Applicant: SHANGHAI UNITED IMAGING HEALTHCARE CO., LTD., Shanghai (CN)

(72) Inventors: Tao Feng, Houston, TX (US); Wentao Zhu, Houston, TX (US); Hongdi Li, Houston, TX (US); Miaofei Han, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 203 days.

(21) Appl. No.: 16/429,246

(22) Filed: Jun. 3, 2019

(65) Prior Publication Data
US 2019/0304144 A1 Oct. 3, 2019

Related U.S. Application Data

(63) Continuation of application No. 15/317,376, filed as application No. PCT/CN2016/089433 on Jul. 8, 2016, now Pat. No. 10,311,604.

(51) Int. Cl.
*G06T 11/00* (2006.01)
*G06T 7/11* (2017.01)
(Continued)

(52) U.S. Cl.
CPC ............ *G06T 11/006* (2013.01); *A61B 5/055* (2013.01); *A61B 6/03* (2013.01); *A61B 6/032* (2013.01);
(Continued)

(58) Field of Classification Search
CPC ......... G06T 2207/10104; G06T 11/003; G06T 2211/424; G06T 7/11; G06T 11/006;
(Continued)

(56) References Cited

U.S. PATENT DOCUMENTS 8,600,136 B2 12/2013 Schweizer et al.
2011/0007958 A1 1/2011 Salomon et al.
(Continued)

OTHER PUBLICATIONS

International Search Report in PCT/CN2016/089433 dated Mar. 30, 2017, 4 pages.
(Continued)

*Primary Examiner* — Kenny A Cese
(74) *Attorney, Agent, or Firm* — Metis IP LLC

(57) ABSTRACT

A method for generating attenuation map is disclosed. The method includes acquiring an anatomic image and PET data indicative of a subject, wherein the anatomic image comprises a plurality of voxels. The method also includes fetching a reference image to register the anatomic image, the reference image includes voxel segmentation information. The method further includes segmenting the anatomic image into a plurality of regions based on the voxel segmentation information. The method further includes generating a first attenuation map corresponding to the anatomic image by assigning attenuation coefficients to the plurality of regions. The method further includes calculating a registration accuracy between the anatomic image and the reference image. The method further includes determining a probability distribution of attenuation coefficient. The method further includes updating the first attenuation map iteratively based on the probability distribution of attenuation coefficient and the PET data to obtain a final attenuation map.

19 Claims, 4 Drawing Sheets

(51) Int. Cl.
- *G06T 7/174* (2017.01)
- *G06T 7/33* (2017.01)
- *A61B 6/00* (2006.01)
- *A61B 6/03* (2006.01)
- *A61B 5/055* (2006.01)

(52) U.S. Cl.
CPC ............ *A61B 6/037* (2013.01); *A61B 6/5205* (2013.01); *A61B 6/5235* (2013.01); *A61B 6/5294* (2013.01); *G06T 7/11* (2017.01); *G06T 7/174* (2017.01); *G06T 7/337* (2017.01); *G06T 2207/10081* (2013.01); *G06T 2207/10088* (2013.01); *G06T 2207/10104* (2013.01); *G06T 2207/20076* (2013.01); *G06T 2207/20221* (2013.01); *G06T 2207/30048* (2013.01); *G06T 2207/30061* (2013.01); *G06T 2207/30096* (2013.01); *G06T 2211/408* (2013.01); *G06T 2211/424* (2013.01)

(58) Field of Classification Search
CPC ......... G06T 7/174; G06T 7/337; A61B 6/037; A61B 6/5205; A61B 6/5235; A61B 6/5294

See application file for complete search history.

(56) References Cited

U.S. PATENT DOCUMENTS

| | | | |
|---|---|---|---|
| 2011/0103669 A1* | 5/2011 | Michel | G06T 11/005 382/131 |
| 2011/0235884 A1* | 9/2011 | Schreibmann | G06T 7/30 382/131 |
| 2013/0266198 A1 | 10/2013 | Pereira et al. | |
| 2015/0117733 A1* | 4/2015 | Manjeshwar | G06T 11/005 382/131 |
| 2017/0032545 A1 | 2/2017 | Mihlin et al. | |

OTHER PUBLICATIONS

Written Opinion in PCT/CN2016/089433 dated Mar. 30, 2017, 4 pages.

* cited by examiner

SYSTEM AND METHOD FOR GENERATING ATTENUATION MAP

CROSS-REFERENCE TO RELATED APPLICATIONS

This application is a continuation application of U.S. patent application Ser. No. 15/317,376, filed on Dec. 8, 2016, which is a U.S. national stage under 35 U.S.C. § 371 of International Application No. PCT/CN2016/089433, filed on Jul. 8, 2016, designating the United States of America, the entire contents of each of which are hereby incorporated by reference.

TECHNICAL FIELD

This application generally relates to the field of attenuation correction in image processing, and specifically, relates to a system and method for attenuation map generation.

BACKGROUND

Emission computed tomography (ECT) includes, for example, a positron emission tomography (PET) system and a single photon emission computed tomography (SPECT) system. The PET system has been applied widely in imaging, especially for medical diagnosis and/or treatment of tumors, heart diseases, brain diseases, etc. A PET system may be integrated with one or more other imaging systems to form a multi-modality system. Exemplary multi-modality systems may include a positron emission tomography-computed tomography (PET-CT) system, a positron emission tomography-magnetic resonance (PET-MR) system, etc. In a PET scan, attenuation to various extents may occur when y-rays pass through different tissues of a subject because the attenuation degrees of different tissues to y-rays are different, causing distortion of a PET image and/or PET data. To reconstruct a PET image and/or PET data, the attenuation may be corrected. An attenuation map may be generated in the process of attenuation correction.

In general, a method based on a CT image may be used to correct the attenuation of a PET image and/or PET data. However, the method based on a CT image (or referred to as a CT-based method) may cause a problem, such as low resolution of soft tissue imaging. A method based on a magnetic resonance (MR) image (or referred to as a MR-based method) may be used to correct the attenuation of a PET image and/or PET data. Compared to a CT-based method, the MR-based method may be provide a high sensitivity and/or high accuracy. However, the MR-based method may have one or more shortcomings in view of at least the followings. There is no mapping relation between the attenuation coefficient distribution of an MR image and the attenuation coefficient distribution of a corresponding PET image. Moreover, there may exist an edge truncation artifact in MR imaging.

Thus, there exists a need in the field to provide a method and system for attenuation correction that may address these and other technical challenges.

SUMMARY

Some embodiments of the present disclosure relate to a method and system for generating an attenuation map. The method may include one or more of the following operations. An anatomic image and PET data indicative of a subject may be acquired. A reference image may be fetched from a database. The reference image may be registered to the anatomic image and include voxel segmentation information. The anatomic image may be segmented into a plurality of regions based on the voxel segmentation information of the reference image. A first attenuation map corresponding to the anatomic image may be generated by assigning attenuation coefficients to the plurality of regions. A registration accuracy between the anatomic image and the reference image may be calculated. A probability distribution of the attenuation coefficient of the voxel of the anatomic image may be determined based on the registration accuracy. The first attenuation map may be updated iteratively based on the probability distribution and the PET data to obtain a final attenuation map.

In some embodiments, the reference images may be fetched based on one or more types of characteristic information of the subject. The characteristic information may include height, weight, gender of the subject, an area of the subject to imaging, or the like, or a combination thereof.

In some embodiments, the determination of the probability distribution of attenuation coefficient may include one or more of the following operations. A statistical probability indicative of a voxel belonging to at least one region of the plurality of regions based on the registration accuracy may be calculated. The probability distribution of attenuation coefficient of the voxel may be acquired based on the statistical probability. If the probability distribution of attenuation coefficient is less than 1, the voxel may be designated belonging to at least two regions of the plurality of regions. If the probability distribution of attenuation coefficient of the voxel is 1, the voxel may be designated belonging to a certain region of the plurality of regions, wherein the certain region of the plurality of regions may comprise a plurality of voxels with a same probability distribution of attenuation coefficient, and the plurality of voxels of the certain region are assigned with a same attenuation coefficient.

In some embodiments, the anatomic image may be a MR image, a CT image, or the like, or any combination thereof.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein.

DETAILED DESCRIPTION

Figure 1:
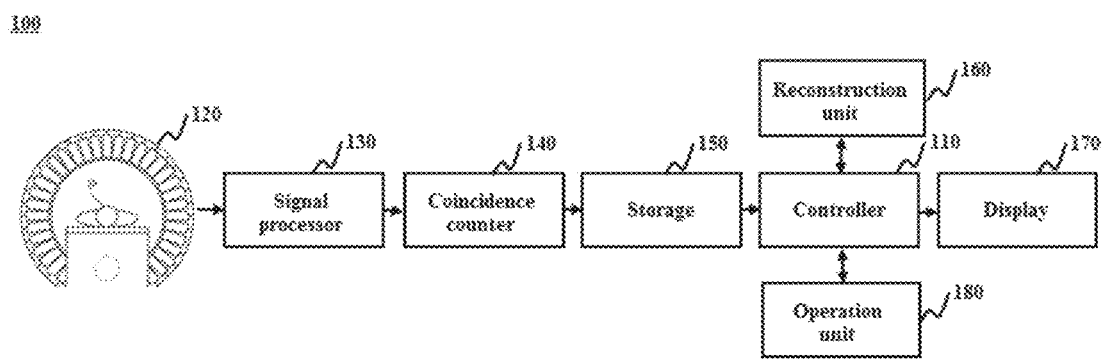
FIG. 1 illustrates an exemplary block diagram of an imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging, such as for disease diagnostic or research purposes. The imaging system may find its applications in different fields such as, for example, medicine or industry. The radiation used herein may include a particle ray, a photon ray, or the like, or any combination thereof. The particle ray may include neutron, proton, electron, µ-meson, heavy ion, or the like, or any combination thereof. The photon beam may include X-ray, γ-ray, α-ray, β-ray, ultraviolet, laser, or the like, or any combination thereof.

Merely by way of example, the imaging system may be a positron emission tomography (PET) system, an emission computed tomography (ECT) system, a multi-modality system, or the like, or any combination thereof. Exemplary imaging systems may include a PET system, a multi-modality system, or the like, or any combination thereof. Exemplary multi-modality systems may include a computed tomography-positron emission tomography (CT-PET) system, a magnetic resonance-positron emission tomography (MR-PET) system, etc.

In a multi-modality system, the mechanisms through which different imaging modalities operate or function may be the same or different. Accordingly, the imaging information may also be the same or different. For example, in some embodiments, the imaging information may be internal and/or external information, and may be functional and/or structural information of a subject. The internal information may be stored in and/or generated by the multi-modality system. The external information may be stored in and/or generated by one or more other imaging systems. In some embodiments, the imaging information of different modalities may complement one another, thereby providing a set of imaging data describing the subject from different analytical angles. For example, in some embodiments, the multi-modality imaging may achieve the merging of morphological and functional images.

In some embodiments, the multi-modality system may include a computed tomography (CT) imaging modality, which is an imaging method that combines multiple X-ray projections taken from different angles to produce detailed cross-sectional images of an internal area of a subject. Thus, CT imaging information may offer medical practitioners precise, three-dimensional views of certain internal parts of the subject, such as soft tissues, bones, blood vessels, organs of a human body, without performing invasive procedures on the subject. In some embodiments, the multi-modality system may include an ultrasound imaging modality, which is an imaging technology that uses high frequency sound waves to create images of the internal of the subject. In some embodiments, the ultrasound imaging modality may send sound waves into the body and convert the returning sound echoes into an image.

In some embodiments of the present disclosure, the multi-modality imaging system may include modules and/or components for performing positron emission tomography (PET) imaging and analysis. The term "positron emission tomography or PET" as used herein refers to a non-invasive radiology procedure applicable to a subject that generates image information reflecting or corresponding to functional processes taking place in the internal body.

During a PET scan or study, PET tracer molecules are first introduced into the subject before an imaging session begins. The term "PET tracer" or "tracer" as used herein refers to a substance that may undergo certain changes under the influence of an activity or functionality within the subject, whose activity and/or functionality are to be visualized and/or studied by the PET. Such changes may be chemical and/or physical, during which the PET tracers may emit positrons, namely the antiparticles of electrons. A positron has the same mass and the opposite electrical charge as an electron, and it undergoes an annihilation with an electron (that may naturally exist in abundance within the subject) as the two particles collide. An electron-positron annihilation may result in two 511 keV gamma photons, which upon their own generation, begin to travel in opposite directions with respect to one another. The PET imaging modules of the present system may obtain the trajectory and/or dose information of the gamma photons to determine the location and concentration of the PET tracer molecules within the subject.

Many basic elements that make up organic matters have positron-emitting isotopes, including carbon ($^{11}C$), nitrogen ($^{13}N$), oxygen ($^{15}O$), and fluorine ($^{18}F$). Accordingly, in some embodiments, the PET tracer molecules of the present disclosure are organic compounds containing one or more of such positron-emitting isotopes. These type of PET tracer molecules are either similar to naturally occurring substances or otherwise capable of interacting with the functionality or activity of interest within the subject. Hence, distributional information of the PET tracer may be reliably used as an indicator of the subject functionality.

Merely by way of example, the PET tracer molecule is $^{18}F$-fluoro-deoxy-glucose ($^{18}F$-FDG), a radioactive analogue of glucose. $^{18}F$-FDG follows a similar metabolic pathway to glucose in vivo, but remains trapped within tissues. Thus, in vivo distribution of $^{18}F$-FDG mapped by the present PET imaging may indicate glucose metabolic activity, which may be of interest in oncology as proliferating cancer cell have higher than average rate of glucose metabolism. Merely by way of example, the PET tracer molecule is $^{13}N$—$NH_3$ for functional imaging of myocardial perfusion. Particularly, in these embodiments, in vivo distribution of $^{13}N$—$NH_3$ may be used to distinguish between viable and non-viable tissue in poorly perfused areas of the heart, which may be of interest in cardiology to identify candidates for coronary by-pass surgery.

Further provided below is a non-exhaustive list of exemplary organic PET tracers that may be used in connection with the present system. In some embodiments, the PET tracer molecule is $^{11}C$-methionine, where it acts as a marker for protein synthesis in oncology. In some embodiments, the PET tracer molecule is $^{11}C$-flumazenil, where it acts as a marker for benzodiazepine receptor activity in epilepsy. In some embodiments, the PET tracer molecule is $^{11}C$-raclopride, where it acts as a marker for D2 receptor agonist activity for diagnosis of movement disorders. In some embodiments, the PET tracer molecule is $^{15}O$-carbon dioxide or $^{15}O$-water, where it acts as a marker for blood perfusion in brains. In some embodiments, the PET tracer is $^{18}F$-fluoride ion, where it acts as a marker for bone metabolism in oncology; in some embodiments, the PET tracer molecule is 18F fluoro-mizonidazole, where it acts as a marker for hypoxia in assessing patient response to radiotherapy in oncology. In some embodiments, multiple different PET tracers may be used in combination to produce complementing sets of functional data.

The above types of imaging modalities that may be included in the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

This is understood that the following descriptions are provided in connection with image processing for illustration purposes and not intended to limit the scope of the present disclosure. The image processing disclosed herein may be used for purposes other than medical treatment or diagnosis. For instance, the image processing may be used for purposes of detecting a fracture within a structure or its progression over time, a non-uniform portion within a piece of material, etc.

For illustration purposes, the following description is provided to help better understanding an image processing. It is understood that this is not intended to limit the scope of some embodiments of the present disclosure. For persons having ordinary skills in the art, a certain amount of variations, changes and/or modifications may be deducted under guidance of some embodiments of the present disclosure. However, those variations, changes and/or modifications do not depart from the scope of some embodiments of the present disclosure.

Some embodiments of the present disclosure relate to image processing. Specifically, some embodiments of the present disclosure relate to a method and system for attenuation map generation and image reconstruction. The process of attenuation map generation and image reconstruction as illustrated in some embodiments of the present disclosure may be automated, or semi-automated. It may be implemented in a computer-aided and automated medical diagnosis and/or treatment system.

FIG. 1 illustrates an exemplary block diagram of an imaging system 100 according to some embodiments of the present disclosure. It should be noted that the imaging system 100 described below is merely provided for illustration purposes, and not intended to limit the scope of the present disclosure. Merely by way of example, the imaging system may be a positron emission tomography (PET) system, a computed tomography (CT) system, a magnetic resonance (MR) system, a multi-modality system, or the like, or any combination thereof. Exemplary multi-modality system may include a computed tomography-positron emission tomography (CT-PET) system, a magnetic resonance-positron emission tomography (MR-PET) system, etc. A subject may be positioned in the PET system, and PET data and/or PET image of the subject may be acquired from the PET system. PET image may be acquired from the reconstruction of PET data.

As shown in FIG. 1, the imaging system 100 may include a controller 110, a gantry 120, a signal processor 130, a coincidence counter 140, a storage 150, a reconstruction unit 160, a display 170, and an operation unit 180. The controller 110 may be configured to control the processing of imaging, the processing of attenuation map generation, the processing of image reconstruction, or the like, or any combination thereof.

The controller 110, the gantry 120, the signal processor 130, the coincidence counter 140, the storage 150, the reconstruction unit 160, the display 170, and the operation unit 180 may be connected with each other. The connection may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), a Wi-Fi, a Wireless a Wide Area Network (WWAN), or the like, or any combination thereof. One or more of the controller 110, the signal processor 130, the coincidence counter 140, the storage 150, the reconstruction unit 160, the display 170 and the operation unit 180 may be integrated in a computer, a laptop, a cell phone, a mobile phone, a portable equipment, a pad, a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an ARM, or the like, or any combination thereof.

The gantry 120 may be configured to generate an electric signal relating to a subject. The term "subject" as used herein may refer to any organic or inorganic mass, natural or man-made, that has a chemical, biochemical, biological, physiological, biophysical and/or physical activity or function. Exemplary embodiments of a subject pertaining to the present disclosure may include cells, tissues, organs or whole bodies of human or animal. Other exemplary embodiments include but not limited to man-made composition of organic and/or inorganic matters that are with or without life. In some embodiments, the subject may be a human patient. The gantry may include a plurality of detector rings. A detector ring may include a plurality of circumferentially arranged detectors. The gantry may detect radiation emitted from a subject to which a radioisotope may be administered by detectors in the detector ring. The gantry may include a field of view (FOV), a subject may be located in the FOV. The subject P may be placed on a patient couch. In some embodiments, a type of PET tracer molecules may be introduced or injected into the subject P for PET imaging. The detector may detect annihilation gamma-rays emitted from inside the subject P to generate an electric signal, which may be in accordance with the quantity of light of the detected pair annihilation gamma-rays.

The signal processor 130 may be configured to generate single event data based on the electric signal generated by detectors of the gantry 102. For purposes of illustration, the signal processor may perform detection time measurement processing, position calculation processing, energy calculation processing, or the like, or any combination thereof. For example, in the detection time measurement processing, the signal processor 130 may measure the detection time of gamma-rays by the detector. More specifically, the signal processor 130 may monitor the peak value of the electric signal generated from the gantry 120. The signal processor 130 may register the time when the peak value of an electric signal exceeds a threshold as a detection time. The signal processor 130 may detect an annihilation gamma-ray by detecting when the amplitude of the electric signal exceeds the threshold. In the position calculation, the signal processor 130 may calculate an incident position of annihilation gamma-rays based on the electric signal. In the energy calculation, the signal processor 130 may determine an energy value of an annihilation gamma-ray incident based on the electric signal. The single event data may be energy values, position coordinates, detection times regarding single events, or the like, or a combination thereof. Single event data may be generated when annihilation gamma-rays are detected. The term "single event" as used herein may refer to the detection of a gamma photon by a detector of the gantry 120.

The coincidence counter 140 may be configured to process single event data relating to a plurality of single events. For the purposes of illustration, the coincidence counter 140 may determine event data of two single events that fall within a preset time interval among continuously supplied single event data. The time interval may be set to, for example, approximately 6 nanoseconds to 18 nanoseconds. A pair of single events detected in the time interval may be deemed to originate from a pair of gamma-rays generated from the same annihilation event. A pair of single events resulting from an annihilation event may be called a coincidence event. The line connecting a pair of the detectors that may detect the coincidence event may be called line of response (LOR). The coincidence counter 140 may count coincidence events for each LOR. Data relating to coincidence events may be referred to as coincidence event data.

The storage 150 may be configured to store data relating to the generation of an attenuation map and/or image processing. The data stored in the storage 150 may include coincidence event data, single event data, a database, imaging data, an attenuation coefficient, an attenuation map, or the like, or any combination thereof. The imaging data may include an MR image, a SPECT image, a PET image, a CT image, or the like, or any combination thereof.

In some embodiments, the database may include one or more anatomic images, voxel segmentation information, or the like, or any combination thereof. In some embodiments, the database may include a plurality of dictionary elements $(D_1, D_2, D_3, \ldots D_X, \ldots, D_{Y-1}, D_Y)$, in which Y may denote the total number of dictionary elements. A dictionary element DX ($1 \leq X \leq Y$) in the database may include two registering images, one of which may be an emission image (which may be denoted as IMGX), one of which may be voxel segmentation information (which may be denoted as $\mathbb{T}_X$, $1 \leq X \leq Y$), or the like, or any combination thereof. In some embodiments, the emission image may include an anatomic image and voxel segmentation information. The anatomic image may include a two-dimensional (2D) image and a three-dimensional (3D) image. The anatomic image may include an emission image, a tomographic image, or the like, or any combination thereof. The anatomic image may include an MR image, a SPECT image, a PET image, a CT image, or the like, or any combination thereof. The emission image may include an MR image, a PET image, a CT image, or the like, or any combination thereof. The characteristic information of the subject indicated by a reference image may include height, weight, gender, age, medical conditions of the subject, medical history of the subject, birthplace of the subject, an area of the subject to imaging, or the like, or any combination thereof. Descriptions regarding a reference image may be found elsewhere in the present disclosure.

In some embodiments, the data stored in the storage 150 may be acquired from one or more of the controller 110, the gantry 120, the signal processor 130, the coincidence counter 140, the reconstruction unit 160, the display 170 and the operation unit 180. Merely by way of example, the data may include the imaging data acquired from the gantry 120. The data may include information and/or instructions acquired from the operation unit 180. The information and/or instructions may include a characteristic information of the subject, a way of displaying, a way of storing, or the like, or any combination thereof. The characteristic information of the subject may include height, weight, gender, age, medical conditions of the subject, medical history of the subject, birthplace of the subject, an area of the subject to imaging, or the like, or any combination thereof. The information of the area of the subject that is imaged may further include the subject position, such as the subject lying pronely or supinely on the couch when the subject is imaged, information of an organ, information of a tissue, or the like, or any combination thereof.

The data stored in the storage 150 may be acquired from or output to an external storage device including, for example, a floppy disk, a hard disk, a CD-ROM, a network server, a cloud server, a wireless terminal, or the like, or any combination thereof. The storage 150 may store data by way of electric energy, magnetic energy, optical energy, or a virtual storage resource, etc. The storage 150 may store data by way of electric energy may include Random Access Memory (RAM), Read Only Memory (ROM), flash memory, or the like, or any combination thereof. The storage 150 may store data by way of magnetic energy may include a hard disk, a floppy disk, a magnetic tape, a magnetic core memory, a bubble memory, a USB flash drive, or the like, or any combination thereof. The storage 150 may store data by way of optical energy may include CD (Compact Disk), VCD (Video Compact Disk), or the like, or any combination thereof. The storage 150 may store data by way of virtual storage resources may include cloud storage, a virtual private network, and/or other virtual storage resources. The method to store data may include sequential storage, link storage, hash storage, index storage, or the like, or any combination thereof.

The reconstruction unit 160 may be configured to reconstruct imaging data. The imaging data may represent the spatial distribution of concentration of a radioisotope inside a subject based on coincidence event data of a plurality of coincidence events. In some embodiment, the imaging data may be PET data of the subject P based on coincidence event data. An emission image may be generated in the reconstruction unit 160 by reconstructing the PET data.

In some embodiment, the reconstruction of the imaging data may be based on time-of-flight (TOF) determination. A detection time difference of a pair of annihilation gamma-rays may be measured and/or recorded by the technique of TOF. The probability of presence of the pair annihilation point in each voxel on the LOR may be different depending on the detection time difference of coincidence events. In some embodiments, an attenuation map may be generated in reconstruction unit 160 to reconstruct the imaging data.

The display 170 may be configured to display one or more images in a display device. The display may include a CRT display, a liquid crystal display, an organic EL display, or plasma display, or the like, or any combination thereof. The display device may include a computer, a laptop, a cell phone, a mobile phone, a portable equipment, a pad, a glass, a projector, a virtual reality device, or the like, or any combination thereof.

The operation unit 180 may be configured to receive one or more information and/or instructions by an operator via an input device. The input device may include a keyboard, a mouse, a button, or a touch key panel, a touch screen, or the like, or any combination thereof. The information and/or instructions may include a characteristic information of the subject, a way of displaying, a way of storing, or the like, or any combination thereof. The characteristic information of the subject may include height, weight, gender, age, medical conditions of the subject, medical history of the subject, birthplace of the subject, an area of the subject to imaging, or the like, or any combination thereof. The information of the area of the subject to imaging may further include the subject position, such as the subject lying pronely or supinely on the couch when the subject is imaged, information of an organ, information of a tissue, or the like, or any combination thereof.

It should be noted that the imaging system described above is merely provided for the purposes of illustration, and not intended to limit the scope of some embodiments of the present disclosure. Apparently for persons having ordinary skills in the art, numerous variations and modifications may be conducted under the teaching of some embodiments of the present disclosure without inventive activity. Some embodiments of the present disclosure is intended to encompass all those variations and modifications as falling under its scope. In some embodiments, the functioning of the storage 150 may be realized in the reconstruction unit 160. Merely by way of example, the database may be stored in the reconstruction unit 160. The information and/or instructions acquired from the operation unit 180 may be stored in the reconstruction unit 160.

Figure 2:
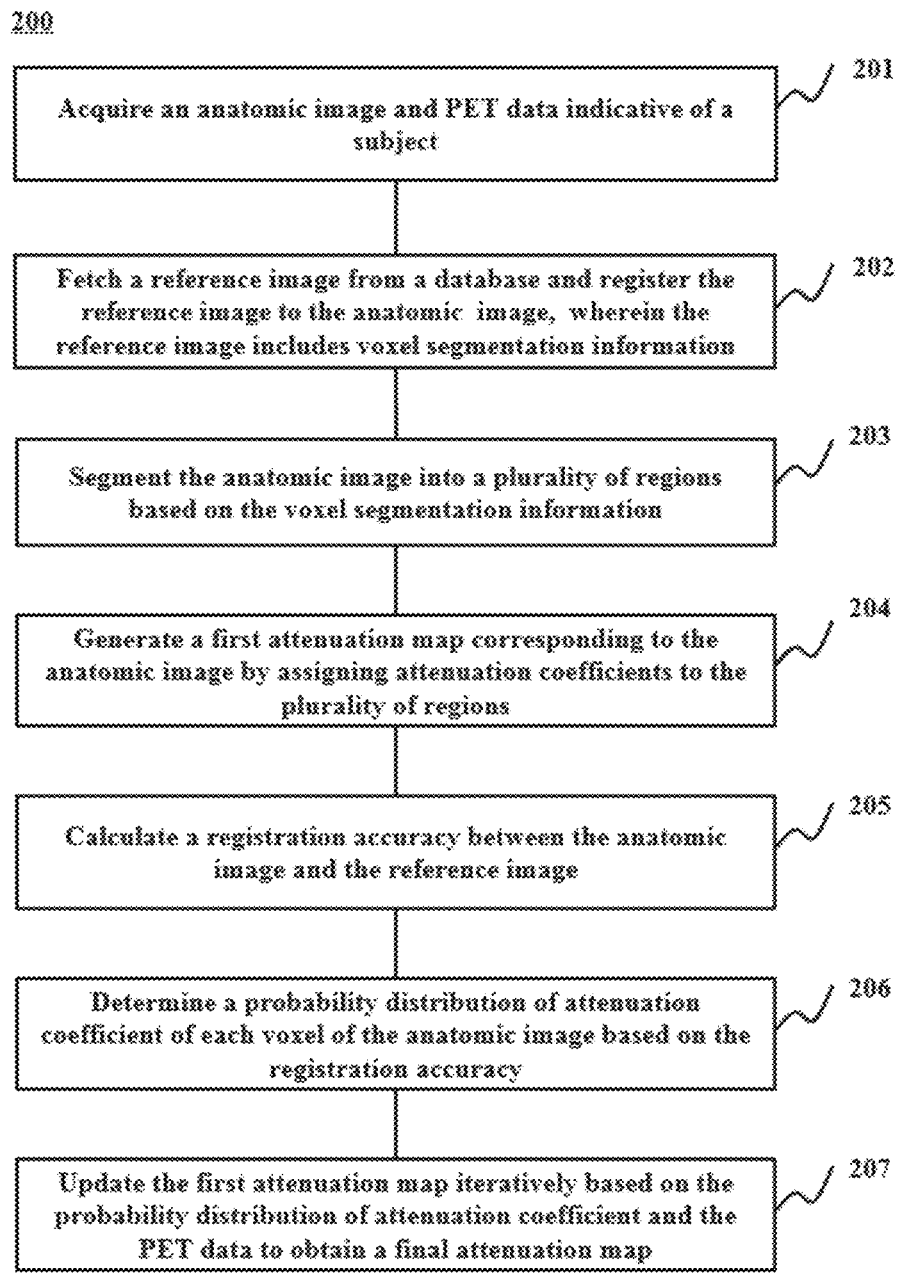
FIG. 2 is an exemplary flowchart illustrating a process for generating an attenuation map according to some embodiments of the present disclosure.

FIG. 2 is an exemplary flowchart illustrating a process for generating an attenuation map according to some embodiments of the present disclosure. In step 201, an anatomic image and PET data indicative of a subject may be acquired, the anatomic image may include a plurality of voxels. The anatomic image may be acquired from the imaging system 100, or acquired from an external memory. The external memory may include a hard disk, a USB flash drive, a cloud storage, a server, or the like, or any combination thereof. The anatomic image may include an MR image, a CT image, or the like, or any combination thereof. The anatomic image may be acquired at a time before step 202 is performed. For example, the anatomic image may be acquired real-timely or not real-timely. Merely by way of example, in the MR-PET system, an MR image may be acquired after the injection of a radioisotope into the subject, and before PET scanning. In some embodiments, the anatomic image may be fetched from the storage 150.

In some embodiments, the MR image(s) may be acquired from a magnetic resonance (MR) system, a magnetic resonance-positron emission tomography (MR-PET) system, a magnetic resonance-single photon emission computed tomography (MR-SPECT) system, or the like, or any combination thereof. In some embodiments, the CT image(s) may be acquired from a computed tomography (CT) system, a computed tomography-positron emission tomography (CT-PET) system, or the like, or any combination thereof.

In step 202, a reference image may be fetched from a database, the reference image may be configured to register the anatomic image. The database may include a plurality of dictionary elements as described in connection with FIG. 1. A dictionary element may include an anatomic image, voxel segmentation information, characteristic information relating to a subject, or the like, or any combination thereof. The characteristic information relating to the subject indicated by the reference image may include height, weight, gender, age, medical conditions of the subject, medical history of the subject, birthplace of the subject, an area of the subject to imaging, or the like, or any combination thereof.

The reference image may be fetched from the database to match the anatomic image. For example, if the characteristic information indicated by the anatomic image matches the characteristic information indicated by the anatomic image of a dictionary element, the anatomic image may be determined as a reference image.

During a diagnosis of a patient, due to the breathing of the patient, peristalsis of the patient's viscera, or an alteration of the patient's position, images obtained for the patient at different times may distort. Images of some viscera for different patients may differ as well. An anatomic image of a dictionary element and an anatomic image may be registered according to various registration methods including, for example, an optical flow method, a registration method based on one or more feature points, a registration method based on a contour, a registration method based on grey scale information, etc.

In some embodiments, an exemplary optical flow process may include one or more of the following operations. An initial deformation field may be specified in the anatomic image and a reference image, respectively. The reference image may be one of image in a dictionary element. The term "deformation field" as used herein may refer to a set of vectors describing how to warp one image to match another.

The initial deformation field may be used for transforming and comparing the anatomic image and the reference image. An updated deformation field of the anatomic image may be calculated based on the optical flow method. An anatomic image (of a dictionary element) may be selected to be used as the reference image based on, for example, a degree of matching with respect to the anatomic image. In some embodiments, the anatomic image (of a dictionary element) that has a highest degree of matching, among the dictionary elements, with respect to the anatomic image may be selected and be designated as the reference image. A deformation field of the selected anatomic image may be calculated based on the optical flow method. The initial deformation field may be updated to generate an updated deformation field. The update may be performed based on, for example, the gradient of the optical flow cost function, etc. The gradient of the optical flow cost function may then be calculated based on the updated anatomic image transformed using the deformation field. The updating of the deformation field and the calculation of the gradient of the optical flow cost function may be iteratively performed until a condition, e.g., convergence, is met.

In some embodiments, a registration method based on feature points may be employed in the present disclosure. For instance, attachment markers may be detected in an anatomic image and a selected anatomic image (of a dictionary element) that has the highest matching degree with the anatomic image, a registration method based on external feature points may be employed. In some embodiments, anchor points or extreme points may be detected in a subject, a registration method based on internal feature points may be employed.

In some embodiments, a registration method based on a contour may be employed. One or more curves and/or the contour of an anatomic image may be extracted; the anatomic image (of a dictionary element) that has a degree of matching with the anatomic image may be selected. For instance, the anatomic image (of a dictionary element) that has a highest degree of matching, among the dictionary elements, with respect to the anatomic image may be selected. One or more corresponding curves and/or the contour of the selected emission image, relative to the anatomic image, may be extracted. Geometric transformation may be determined based on the extracted curves and/or contour.

In some embodiments, a registration method based on grey scale information of one or more pixels may be employed in the present disclosure. For instance, statistic information of images, mutual information, grey space entropy, etc., may be employed to obtain a reference image of an anatomic image.

A dictionary element of the database may include an anatomic image and voxel segmentation information corresponding to the anatomic image. According to the reference image determined in step 202, the voxel segmentation information corresponding to the reference image may be acquired. The registration methods described above and other registration methods may be used to register the anatomic image and the reference image. For example, the registration method may be based on Atlas registration.

In step 203, the anatomic image may be segmented into a plurality of regions based on the voxel segmentation information of the reference image. In step 204, a first attenuation map corresponding to the anatomic image may be generated by assigning attenuation coefficients to the plurality of regions (e.g., a spatial region, which may be also referred to as a geometrical region, etc.). The attenuation coefficients may be stored in the database, and the attenuation coefficients may correspond to one or more spatial regions. In some embodiments, the attenuation coefficients may be acquired from a user and/or input by the user. A spatial region may be a bone, a tissue, an organ, a vessel, viscera, or the like, or any combination thereof. Merely by way of example, the voxel segmentation information of a dictionary element that has the highest degree of matching with respect to the patient's physiological information may be distorted to provide voxel segmentation information of the anatomic image. For example, a distortion field may be obtained to register an anatomic image and an anatomic image of the dictionary, and the distortion field may be applied to the voxel segmentation information of the anatomic image to generate voxel segmentation information of the anatomic image. The voxel segmentation information of the anatomic image may be used to segment the anatomic image into a plurality of regions. The voxel segmentation of an anatomic image may be based on segmentation, and the voxels of the anatomic image may be segmented into a plurality of regions ($S_1$, $S_2$, $S_3$, . . . , $S_{Q-1}$, $S_Q$) based on segmentation and registration, in which Q (Q>1) may denote the number of regions. The plurality of regions may include at least some of the voxels of the anatomic image.

On the basis of the plurality of regions and the topological information of the voxels of the anatomic image, the voxel segmentation information of a dictionary element may include corresponding attenuation coefficients. The attenuation coefficients corresponding to voxels of the plurality of regions may be determined based on the attenuation coefficients of the dictionary element. For example, some voxels of the anatomic image may be segmented and designated as a bone region, and the attenuation coefficient of a bone of the dictionary element may be assigned to the bone region of the anatomic image. As another example, some voxels of an anatomic image may be segmented and designated as a lung tissue, and the attenuation coefficient of lung tissue of the dictionary element may be assigned to the lung tissue of the anatomic image.

Figure 3A:
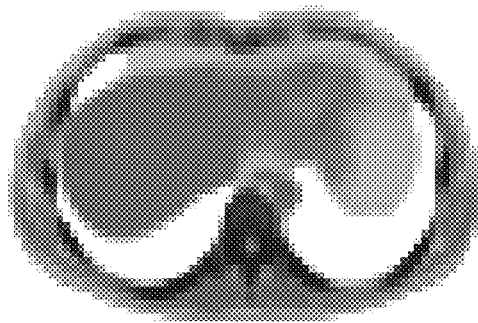
FIG. 3A is an exemplary attenuation map of transverse section of the region between the lungs and the abdomen of a subject generated by a PET scan according to some embodiments of the present disclosure.

FIG. 3A illustrates an attenuation map of a transverse section of the region between the lungs and the abdomen of a subject generated by a PET scan. Due to the variations of absorption of photons by different portions of a human body, the attenuation effect by different portions of the human body may be different (e.g., different grey value corresponding to different attenuation coefficients). For example, the portion with a higher grey value may correspond to right lobe of liver, and the portion with a lower grey value may correspond to stomach. The white portion may correspond to a portion of lung, and the black portion may correspond to a portion of bone.

Figure 3B:
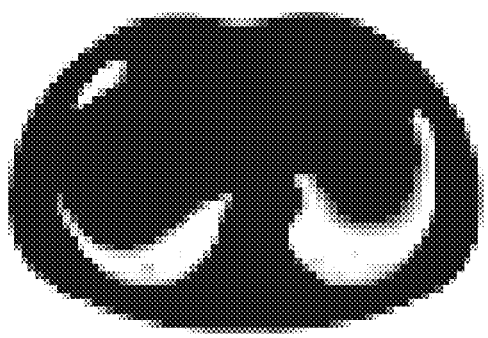
FIG. 3B is an exemplary first attenuation map of transverse section of the region between the lungs and the abdomen of the same subject as in FIG. 3A according to some embodiments of the present disclosure.

FIG. 3B illustrates an initial attenuation map of a transverse section of the region between the lungs and the abdomen of the same subject as in FIG. 3A. Two levels of grey value may be seen in FIG. 3B, suggesting that 2 attenuation coefficients may be associated with the image. The attenuation coefficient of the liver, the stomach, and the spleen may be similar or essentially the same. As used herein, "essentially," as in "essentially the same," "essentially approximate," etc., with respect to a parameter or a characteristic may indicate that the variation is within 2%, or 5%, or 8%, or 10%, or 15%, or 20% of the parameter or the characteristic. As shown in FIG. 3B, it may be difficult to recognize the boundary regions between organs and/or tissues.

Figure 3C:
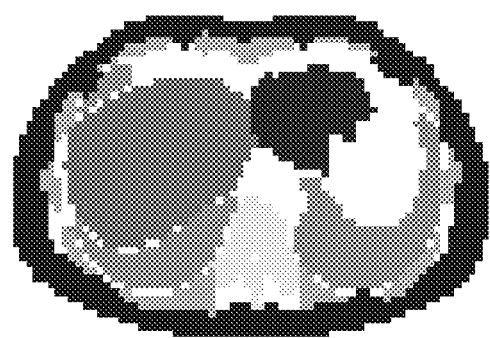
FIG. 3C is an exemplary attenuation map that generated by segmenting an anatomic image into a plurality of regions based on voxel segmentation information of a reference image according to some embodiments of the present disclosure.

FIG. 3C illustrates an attenuation map that generated based on segmenting an anatomic image into a plurality of regions based on the voxel segmentation information of a reference image. As shown in FIG. 3C, different portions may have different grey values (different attenuation coefficients). The shape of each organ may be difficult to be identified. The boundary regions of lung and liver may include voxels whose belongings are not determined. The boundary regions of lung and bone may include voxels whose belongings are not determined as well. Meanwhile the boundary of the organs is not clear. The attenuation map that is generated based on segmenting an anatomic image into a plurality of regions based on the voxel segmentation information of a reference image may essentially approximate that shown in FIG. 3C. Due to the restriction caused by the accuracy of a registration method, it may be difficult to determining which regions a voxel at a boundary region belong to. Therefore, a probability distribution of attenuation coefficients of voxels may be employed in the present disclosure to refine the plurality of regions as described above, and determine which regions the voxels of boundary regions belong to.

In step 205, the registration accuracy between the anatomic image and the reference image may be calculated. The registration accuracy may be calculated based on mutual information (MI) between the anatomic image and the reference image, variance between the anatomic image and the reference image, or the like, or any combination thereof.

In some embodiments, the registration accuracy may be determined with a formula of:

$$R(A(x,y,z), M(x,y,z)) = \left\| \left( A(x,y,z) - \frac{\int_{v \in S} A(x,y,z)dv}{\int_{v \in S} dv} \right) \times \left( M(x,y,z) - \frac{\int_{v \in S} M(x,y,z)dv}{\int_{v \in S} dv} \right) \right\|,$$ (Formula 1)

in which A may denote the reference image, M may denote the anatomic image indicative of the subject, R (A, M) may denote the registration accuracy between the reference image A and the anatomic image M; S may denote the plurality of regions ($S_1$-$S_M$) generated in step 203; v may denote all the voxels of a certain region of the regions from $S_1$ to $S_Q$, wherein the certain region comprise a plurality of voxels. ‖ ‖ may denote an absolute value function; (x, y, z) may denote three-dimensional coordinate of a voxel in the plurality of regions, x may denotes x-axis coordinate, y may denote y-axis coordinate, and z may denote z-axis coordinate.

For the purposes of illustration, the registration accuracy may show a degree of similarity between the reference image A and the anatomic image M. The reference image A and the anatomic image M may be of a same type. For instance, both the reference image A and the anatomic image M may be MR images, CT images etc. The reference image A and the anatomic image M may be of different types. For instance, the reference image A and the anatomic image M may be an MR image and a CT image, respectively.

In step 206, the probability distribution of attenuation coefficients of voxels of the anatomic image may be determined based on the registration accuracy. The term "probability distribution of attenuation coefficient" may refer to the probability distribution of different attenuation coefficients of a voxel. In some embodiments, the probability distribution of various attenuation coefficients of a voxel $\vec{r}$ may be determined, in which the probability $P(\mu_j)$ for an attenuation coefficient $\mu_j$ may be determined with a formula of:

$$P(\mu_j) = \Sigma_w P(\vec{r} \in S_w) G(\mu_j - U_w).$$ (Formula 2)

In Formula 2, $\mu_j$ may denote an attenuation coefficient of a voxel $\vec{r}$; $P(\mu_j)$ may denote a probability of the attenuation coefficient $\mu_j$ of the voxel $\vec{r}$; $P(\vec{r} \in S_w)$ may denote a statistical probability of the voxel belonging to a certain region $S_w$; $U_w$ may denote the attenuation coefficient of region $S_w$; and G may denote a Gaussian distribution function (often simply referred to as a Gaussian or a Gaussian function). It should be noted that the certain region may comprise a plurality of voxels with a same probability distribution of attenuation coefficient, and the plurality of voxels of the certain region may be assigned with a same attenuation coefficient.

In some embodiments, the probability distribution of attenuation coefficient of a voxel may be determined with a formula of:

$$P(\mu_j) = \Sigma_w f_1(P(\vec{r} \in S_w)) G(\mu_j - U_w f_2(P(\vec{r} \in S_w))),$$ (Formula 3)

in which $\mu_j$ may denote an attenuation coefficient of a voxel $\vec{r}$; $P(\mu_j)$ may denote a probability distribution of attenuation coefficient of the voxel $\vec{r}$; $P(\vec{r} \in S_w)$ may denote a statistical probability of the voxel belonging to a certain region $S_w$; the certain region $S_w$ may be a spatial region; $U_w$ may denote an attenuation coefficient corresponding to the region $S_w$ which the voxel $\vec{r}$ belongs to; $f_1(x)$ may denote an increasing function, in which $x \in [0, 1]$; and $G(\mu_j - U_w, f_2(P(\vec{r} \in S_w)))$ may denote a Gaussian function, with a variance $f_2(P(\vec{r} \in S_w))$, in which $f_2(x)$ may denote a decreasing function, wherein $x \in [0, 1]$.

The statistical probability of a voxel belonging to a certain region (often simply referred to as $P(\vec{r} \in S_w)$) may be used to calculate $P(\mu_j)$. $P(\vec{r} \in S_w)$ may be determined with a formula of:

$$P(\vec{r} \in S_w) = \frac{\int_{v \in V(\vec{r})} R(A, M) dv}{\sqrt{\int_{v \in V(\vec{r})} R(A, A) dv * \int_{v \in V(\vec{r})} R(M, M) dv}},$$ (Formula 4)

in which $\vec{r}$ may denote a voxel of the plurality of regions of the anatomic image, $V(\vec{r})$ may denote a three-dimensional (3D) region (such as a spatial region), and the voxel $\vec{r}$ may be the center of $V(\vec{r})$; $S_w$ may denote a region of the plurality of regions of the reference image A. $P(\vec{r} \in S_w)$ may denote the statistical probability of the voxel $\vec{r}$ belonging to a certain region Sw ($1 \leq w \leq Q$).

When the reference image A and the anatomic image M in the region of $V(\vec{r})$ are totally same or proportionally same, $P(\vec{r} \in S_w) = 1$, which may indicate that the voxel $\vec{r}$ belongs to the region $S_w$, and further indicate that voxel segmentation information of the anatomic image M may be same to voxel segmentation information of the reference image. When the reference image A and the anatomic image M in the region of $V(\vec{r})$ are not same or not proportionally same, $0 < P(\vec{r} \in S_w) < 1$, which may indicate that the voxel $\vec{r}$ may belong to N regions (1<N≤m), the statistical probability of the voxel $\vec{r}$ belonging to the region $S_w$ is $P(\vec{r} \in S_w)$ and $\Sigma_{w=1}^{N} P(\vec{r} \in S_w)=1$, in which N may denote a total number of regions which the voxel $\vec{r}$ may belong to. For example, when the reference image A and the anatomic image M in the region of $V(\vec{r})$ are not the same, the voxel $\vec{r}$ may belong to two regions (such as a region $S_1$ and a region $S_2$); the statistical probability of the voxel $\vec{r}$ belonging to the region $S_1$ is $P(\vec{r} \in S_1)=0.8$ and, the probability of the voxel $\vec{r}$ belonging to the region $S_2$ is $P(\vec{r} \in S_2)=0.2$.

For the purposes of illustration, the voxels of the anatomic image indicative of the subject belonging may be classified into two groups (e.g., one kind is a confirmed group, and the other kind is an unconfirmed group) based on the registration accuracy. The voxels in the confirmed group may be located inside one region. The voxel in the unconfirmed group may be located at a boundary region of one or more regions, and thus the classification of the voxels of boundary regions may need to be further analyzed.

In step 207, the first attenuation map as described in step 204 may be updated iteratively to generate a final attenuation map. The first attenuation map may be updated based on the probability distribution of attenuation coefficient of voxels and PET data of the subject.

In some embodiments, a second attenuation map may be generated to obtain the final attenuation map. In some embodiments, in an initial stage the first attenuation map generated in step 204 may be fixed, the PET data may be updated based on the first attenuation map to generate PET data for a first PET image, then the contribution of the first PET image in data field may be calculated, and the first attenuation map may be updated to generate a second attenuation map based on the contribution of the first image in data field, for example, updating the attenuation coefficient of each of the plurality of the regions of the anatomic image.

$$\mu_j^{(n,m+1)} = \mu_j^{(n,m)} - \frac{\frac{\partial \tilde{L}(\mu, f, p)}{\partial \mu_j}\bigg|_{\mu_j^{(n,m)}}}{\sum_k \frac{\partial^2 \tilde{L}(\mu, f, p)}{\partial \mu_j \partial \mu_k}\bigg|_{\mu_j^{(n,m)}}}, \quad \text{(Formula 5)}$$

wherein $\mu_j^{(n,m+1)}$ may denote the attenuation coefficient generated based on updating the attenuation coefficient $\mu_j^{(n,m)}$ of voxel. n may denote the index number of iteration, m may denote the index number of sub-iteration, and j may denote the index number of voxel. $\mu_j^{(n,m+1)}$ may be obtained based on $\mu_j^{(n,m)}$ by performing the n-th iteration and the m-th sub-iteration on voxel j. $\mu_j^{(n,m)}$ may denote the attenuation coefficient before performing the n-th iteration and the m-th sub-iteration on voxel j. The initial value of $\mu_j^{(n,m)}$ may be assigned based on prior knowledge, for example, based on reference images stored in the database as described elsewhere in the present disclosure. In some embodiments, the attenuation coefficients of the voxels of the unconfirmed group may be iteratively updated based on probability distribution of attenuation coefficient and PET data, the attenuation coefficients of the voxels of the confirmed group may be iteratively updated based on PET data solely. In some embodiments, for some voxels, one iteration is sufficient. For other voxels, for example, voxels in the boundary regions, multiple iterations may be performed to generate a final attenuation map. As an example of the second iteration, PET data of a second PET image may be generated by updating the PET data of the first PET image based on the second attenuation map. The contribution of the second PET image in data field may be calculated, and a third attenuation map may be generated by updating the second attenuation map based on the contribution of the second PET image in data field.

In some embodiments, the first attenuation map may be continuously updated during a reconstruction of the PET data. The reconstruction of the PET data may be based on a time-of-flight (TOF) technique. A detection time difference of a pair of annihilation gamma-rays may be measured and/or recorded by a TOF based method. The probability of presence of the pair annihilation point in each voxel on the line of response (LOR) may be different depending on the detection time difference of coincidence events. For example, TOF-PET scan may measure the time difference between the detection of two 511 keV annihilation photons.

For the purposes of illustration, taking a reconstruction of the PET data acquired from the PET system for example, the PET data acquired from the PET system may be updated based on an ordered-subset expectation maximization (OSEM) method. An updating PET data and/or PET image based on the OSEM method may be expressed with a formula of:

$$f_j^{(n,m+1)} = \frac{f_j^{(n,m)}}{\sum_{t,i \in S_m} \overline{a}_i^{(n,m)} H_{ijt}} \quad \text{(Formula 6)}$$

$$\sum_{t,i \in S_m} H_{ijt} \frac{1/\varepsilon_i(t)}{\sum_{k,t} H_{ikt} f_k^{(n,m)} + \frac{s_i(t) + r_i(t)}{\overline{a}_i^{(n,m)}}},$$

in which $\overline{a}_i^{(n,m)}$ may denote the i-th element of an attenuation sinogram, the attenuation sinogram may be acquired after n iterations to a m-th sub-iteration of a subset, and an initial value of $\overline{a}_i^{(n,m)}$ may be determined based on an attenuation coefficient of a region; In some embodiments, $\overline{a}_i^{(n,m)}$ may equal to $e^{-\Sigma_j l_{ij} u_j^{(n,m)}}$ ($\overline{a}_i^{(n,m)} = e^{-\Sigma_j l_{ij} u_j^{(n,m)}}$), $l_{ij}$ may denote the system array of linear integral model that maps an attenuation map to an attenuation sinogram, $\mu_j^{(n,m)}$ may denote the attenuation coefficient before performing the n-th iteration and the m-th sub-iteration on voxel j; $f_j^{(n,m+1)}$ may denote PET data and/or PET image acquired in the n-th iteration to the m-th sub-iteration of subset, $f_j^{(n,m)}$ may denote PET data and/or PET image before performing the n-th iteration and m-th sub-iteration of voxel j; $S_m$ may denote a m-th data subset in data space; $H_{ijt}$ and $H_{ikt}$ may respectively denote a system matrix; i may denote the index number of LOR; k may denote the k-th voxel of PET data and/or PET image; j may denote the j-th voxel of PET data and/or PET image; t may denote the index number of TOF bin; $\varepsilon_i(t)$ may denote the normalized coefficient to a listmode data on a i-th LOR of a t-th TOF bin; $s_i(t)$ may denote the number of scattering coincidence events on a i-th LOR of a t-th TOF bin; $r_i(t)$ may denote the number of random coincidence events on a i-th LOR of a t-th TOF bin.

The contribution of the PET data in data field may be calculated. An expectation of a voxel of a TOF sinogram may be determined with a formula of:

$$\overline{y}_i^{(n,m+1)} = \overline{a}_i^{(n,m)} \Sigma_{j,t} H_{ijt} f_j^{(n,m+1)}, \quad \text{(Formula 7)}$$

where $\overline{y}_i^{(n,m+1)}$ may denote an expectation of a voxel of a TOF sinogram, the voxel may be one voxel in a PET image, which may have been performed a n-th iteration and a m-th sub-iteration.

A probability function may be used to reconstruct the PET data. For example, the probability function may be a likelihood function, such as a penalized likelihood function, which may be shown with a formula of:

$$\mathcal{L}(\mu, f, p) = \Pi_i (\hat{p}_i)^{p_i} (p_i!)^{-1} \exp(-\hat{p}_i), \quad \text{(Formula 8)}$$

where $$\hat{p}_i = \Sigma_j H_{i,j} f_j e^{-\Sigma_j l_{i,j} \mu_j} + s_i + r_i, \quad \text{(Formula 9)}$$

In Formula 9, $\hat{p}_i$ and/or p may denote originally acquired coincidence event; i may denote the index number of LOR and/or TOF; j may denote the j-th voxel of an PET image, which may be acquired from the PET data; $s_i$ may denote the number of scattering coincidence events; $r_i$ may denote the number of random coincidence events; $H_{i,j}$ may denote system response matrix including TOF information; $l_{i,j}$ may denote a system matrix of a line integral, which may be generated from an attenuation map mapping to an attenuation sinogram. A likelihood function with a parameter of probability distribution of attenuation coefficient (such as $P(\mu_j)$) may be shown with a formula of:

$$\hat{\mathcal{L}}(\mu, f, p) = \Pi_i (\hat{p}_i)^{p_i} (p_i!)^{-1} \exp(-\hat{p}_i) \Pi_j (P(\mu_j)), \quad \text{(Formula 10)}$$

A log-likelihood function of the formula 7 may be shown with a formula of:

$$\tilde{L}(\mu, f, p) = \Sigma_i p_i \log(\hat{p}_i) - \hat{p}_i + \mathbb{P}(\mu_j), \quad \text{(Formula 11)}$$

where $\mathbb{P}(\mu_j) = \Sigma_j \log(P(\mu_j))$.

An updated attenuation coefficient based on the OSEM mothed may be determined with a formula of:

$$\mu_j^{(n,m+1)} = \mu_j^{(n,m)} + \quad \text{(Formula 12)}$$

$$\frac{\sum_{i \in S_m} l_{ij} \frac{\overline{y}_i^{(n,m+1)}}{\overline{y}_i^{(n,m+1)} + s_i + r_i} (\overline{y}_i^{(n,m+1)} + s_i + r_i - y_i) - \frac{\partial \mathbb{P}(\mu)}{\partial \mu_j}\bigg|_{\mu_j^{(n,m)}}}{\sum_{i \in S_m} l_{ij} \frac{(\overline{y}_i^{(n,m+1)})^2}{\overline{y}_i^{(n,m+1)} + s_i + r_i} \Sigma_k l_{ik} + \sum_k \frac{\partial^2 \mathbb{P}(\mu)}{\partial \mu_j \partial \mu_k}\bigg|_{\mu_j^{(n,m)}}},$$

where $\mu_j^{(n,m+1)}$ may denote the attenuation coefficient generated based on updating the attenuation coefficient $\mu_j^{(n,m)}$. n may denote the index number of iteration, m may denote the index number of sub-iteration, and j may denote the index number of voxel. $\mu_j^{(n,m+1)}$ may be obtained based on $\mu_j^{(n,m)}$ by performing the n-th iteration and the m-th sub-iteration on voxel j. $\mu_j^{(n,m)}$ may denote the attenuation coefficient before performing the n-th iteration and the m-th sub-iteration on voxel j. The initial value of $\mu_j^{(n,m)}$ may be assigned based on prior knowledge, for example, based on reference images stored in the database as described elsewhere in the present disclosure. $l_{i,j}$ may denote a system matrix of a line integral, referring to the length of the i-th LOR through the voxel j, which may be generated from an attenuation map corresponding to an attenuation coefficient; $y_i$ may denote the number of annihilation photon pairs acquired from the i-th LOR; $s_i$ may denote the number of scattering coincidence events acquired from the i-th LOR; $r_i$ may denote the number of random coincidence events acquired from the i-th LOR; $\overline{y}_i^{(n,m+1)}$ may denote an expectation of i-th voxel of a PET image in TOF sinogram, the PET image may have been performed a n-th iteration and a m-th sub-iteration. It should be noted that, in some embodiments, voxels in a same region may be assigned with a same attenuation coefficient, the iterative updating of the attenuation coefficients may be performed to the attenuation coefficients assigned to the plurality of regions, rather than be performed to all attenuation coefficients of the voxels of the plurality of regions. In some embodiments, one or more iterations may be performed. In some embodiments, keeping a first PET attenuation image (also referred to as a first attenuation map of PET image) fixed, an iteration may be performed to PET data to acquire a PET image. Keeping the PET image fixed, an iteration may be performed to the attenuation coefficients of the first PET attenuation image to acquire a second PET attenuation image. In one iteration, each subset in data space corresponding to the first PET attenuation image may be traversed. Then, another iteration may be performed until a criterion is satisfied and the iteration may terminate. For instance, the criterion may be that attenuation coefficient acquired in the n-th iteration is the same as the attenuation coefficient acquired in the (n+1)-th iteration. If the criterion is not satisfied, a next iteration may be performed. The next iteration may take result of last iteration as initial.

In some embodiments, an attenuation map and a PET image may be updated alternatively. For example, the attenuation map may be updated while keeping the PET image fixed to generate a second attenuation map, and then the PET image may be updated while keeping the second attenuation map fixed to generate a second PET image. The second attenuation map may be updated while keeping the second PET image fixed. It should be noted that for the voxels located in a region of the plurality of regions, one iteration may be sufficient. For the voxels located in boundary regions of multiple regions of the plurality of regions (e.g., the voxels of the unconfirmed group), multiple iterations may be performed to determine the belongings of the voxels. For example, designating a voxel located in the boundary regions as belonging to a certain regions of the plurality of regions.

In some embodiments, the reconstruction of a PET image may be performed based on the following operations. The PET image may be acquired by reconstructing PET data, and the PET data may be attenuation corrected by an attenuation map, the attenuation map may be generated based on the following steps.

Acquiring an anatomic image indicative of a subject, the anatomic image may be an MR image or a CT image; fetching a reference image from a database, the reference image may include voxel segmentation information; registering the reference image to the anatomic image; Segmenting the anatomic image into a plurality of regions based on the voxel segmentation information of the reference image; generating a first attenuation map corresponding to the anatomic image by assigning attenuation coefficients to the plurality of regions. The voxels belonging to one region of the plurality of regions may be assigned with a same attenuation coefficient. Updating the PET data based on the first attenuation map to generate PET data for a first PET image.

Acquiring probability distribution of attenuation coefficient of voxels of the plurality of regions, and dividing the voxels of the plurality of regions into two groups, confirmed group and unconfirmed group. The voxels whose probability distribution is 1 may be designated as belonging to a certain region of the plurality of regions. Probability distribution of attenuation coefficient of the voxels of the unconfirmed group may be less than 1, and the voxels of the unconfirmed group may be designated as belonging to at least two regions of the plurality of regions. Probability distribution of attenuation coefficient may be obtained based on the following steps: calculating the registration accuracy of the anatomic image and the reference image, and calculating probability distribution of attenuation based on the registration accuracy. The term "probability distribution of attenuation coefficient" may refer to the probability distribution of the attenuation coefficient of a voxel of the plurality of regions.

For the voxels of the unconfirmed group, updating the first attenuation map based on the probability distribution of attenuation coefficient of voxels and the updated PET data to obtain a second attenuation map. Obtaining a final attenuation map based on the second attenuation map. For the voxels of confirmed group, the first attenuation map may be updated solely based on the PET data. In some embodiments, the first attenuation map may be updated based on probability distribution of attenuation coefficient of voxels and the updated PET data, and a second attenuation map may be generated. A final attenuation map may be obtained based on the second attenuation map. In some embodiments, multiple iterations may be performed to obtain the PET image and the final attenuation map.

Figure 3D:
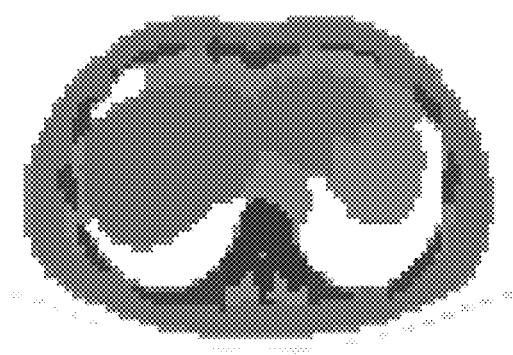
FIG. 3D is an exemplary final attenuation map of transverse section of the region between the lungs and the abdomen of the same subject as in FIG. 3A and FIG. 3B according to some embodiments of the present disclosure.

FIG. 3D illustrates a final attenuation map of transverse section of the region between lung and abdomen according to some embodiments of the present disclosure, which may be similar to the actual attenuation map of the transverse section of the region between the lungs and the abdomen of the subject as shown by FIG. 3A.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, step 201, step 202, step 203, step 204, step 205, step 206 and step 207 may be performed sequentially at an order other than that described above in FIG. 2. Step 201, step 202, step 203, step 204, step 205, step 206 and step 207 may be performed concurrently or selectively. Step 201, step 202, step 203, step 204, step 205, step 206 and step 207 may be merged into a single step or divided into a number of steps. In addition, one or more other operations may be performed before/after or in performing step 201, step 202, step 203, step 204, step 205, step 206 and step 207.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing apparatus having at least one processor and at least one computer-readable storage device, the method comprising:
   acquiring listmode positron emission tomography (PET) data of a subject;
   acquiring an initial attenuation map of the subject for PET reconstruction;
   during one or more iterations,
      generating a PET image based on an attenuation map and the listmode PET data, the attenuation map including the initial attenuation map or an updated attenuation map from a previous iteration,
      determining contribution of the listmode PET data in data field based on the PET image, and
      updating the attenuation map to obtain an updated attenuation map based on the contribution of the listmode PET data in data field, comprising:
         determining a probability distribution of an attenuation coefficient of each voxel of the attenuation map; and
         updating the attenuation map to obtain an updated attenuation map based on the contribution of the listmode PET data in data field and the probability distribution of attenuation coefficient of the voxel; and
   designating the attenuation map in a last iteration as the final attenuation map.

2. The method of claim 1, wherein the acquiring the initial attenuation map of the subject for PET reconstruction comprising:
   acquiring an anatomic image indicative of the subject, wherein the anatomic image comprises a plurality of voxels;
   fetching a reference image from a database, wherein the reference image comprises voxel segmentation information;
   registering the reference image to the anatomic image;
   segmenting the anatomic image into a plurality of regions based on the voxel segmentation information of the reference image;
   generating the initial attenuation map by assigning attenuation coefficients to the plurality of regions of the anatomic image.

3. The method of claim 2, wherein the anatomic image is a magnetic resonance (MR) image or a computed tomography (CT) image.

4. The method of claim 2, the fetching the reference image is based on one or more types of characteristic information of the subject.

5. The method of claim 4, wherein the one or more types of characteristic information comprise height, weight, gender of the subject, or an area of the subject to imaging.

6. The method of claim 2, the registering the reference image to the anatomic image is based on at least one of optical flow, feature points, a contour, or grey scale information.

7. The method of claim 1, the determining the probability distribution of the attenuation coefficient of the voxel comprising:
   calculating a statistical probability indicative of the voxel belonging to a certain region of the plurality of regions based on the registration accuracy; and
   acquiring the probability distribution of the attenuation coefficient of the voxel based on the statistical probability.

8. The method of claim 7, further comprising designating, if the statistical probability is 1, the voxel as belonging to the certain region of the plurality of regions.

9. The method of claim 8, wherein the certain region of the plurality of regions comprises a plurality of voxels with a same probability distribution of attenuation coefficient, and the plurality of voxels of the certain region are assigned with a same attenuation coefficient.

10. The method of claim 7, further comprising designating, if the statistical probability is less than 1, the voxel as belonging to at least two regions of the plurality of regions.

11. The method of claim 10, wherein the voxel is designated as belonging to one region of the at least two regions as the final attenuation map is obtained.

12. An imaging system comprising:
a storage configured to store a set of instructions;
at least one processor in communication with the storage, wherein when executing the instructions, the at least one processor is configured to cause the imaging system to:
acquire listmode PET data of a subject;
acquire an initial attenuation map of the subject for PET reconstruction;
during one or more iterations,
  generate a PET image based on an attenuation map and the listmode PET data, the attenuation map including the initial attenuation map or an updated attenuation map from a previous iteration,
  determine contribution of the listmode PET data in data field based on the PET image, and
  update the attenuation map to obtain an updated attenuation map based on the contribution of the listmode PET data in data field, the at least one processor is configured to cause the imaging system further to:
    determine a probability distribution of an attenuation coefficient of each voxel of the attenuation map; and
    update the attenuation map to obtain an updated attenuation map based on the contribution of the listmode PET data in data field and the probability distribution of attenuation coefficient of the voxel; and
designate the attenuation map in a last iteration as the final attenuation map.

13. The system of claim 12, wherein to acquire the initial attenuation map of the subject for PET reconstruction, the at least one processor is configured to cause the imaging system further to:
acquire an anatomic image indicative of the subject, wherein the anatomic image comprises a plurality of voxels;
fetch a reference image from a database, wherein the reference image comprises voxel segmentation information;
register the reference image to the anatomic image;
segment the anatomic image into a plurality of regions based on the voxel segmentation information of the reference image;
generate the initial attenuation map by assigning attenuation coefficients to the plurality of regions of the anatomic image.

14. The system of claim 13, wherein to fetch the reference image is based on one or more types of characteristic information of the subject.

15. The system of claim 14, wherein the one or more types of characteristic information comprise height, weight, gender of the subject, or an area of the subject to imaging.

16. The system of claim 12, wherein to determine the probability distribution of the attenuation coefficient of the voxel, the at least one processor is configured to cause the imaging system further to:
calculate a statistical probability indicative of the voxel belonging to a certain region of the plurality of regions based on the registration accuracy; and
acquire the probability distribution of the attenuation coefficient of the voxel based on the statistical probability.

17. The system of claim 16, wherein the at least one processor is configured to cause the imaging system further to designate, if the statistical probability is 1, the voxel as belonging to the certain region of the plurality of regions.

18. The system of claim 17, wherein the certain region of the plurality of regions comprises a plurality of voxels with a same probability distribution of attenuation coefficient, and the plurality of voxels of the certain region are assigned with a same attenuation coefficient.

19. The system of claim 16, wherein the at least one processor is configured to cause the imaging system further to designate, if the statistical probability is less than 1, the voxel as belonging to at least two regions of the plurality of regions and the voxel is designated as belonging to one region of the at least two regions as the final attenuation map is obtained.

* * * * *